United States Patent
Kishan

(10) Patent No.: US 9,861,389 B2
(45) Date of Patent: Jan. 9, 2018

(54) BILATERAL CONTOURED ROD AND METHODS OF USE

(71) Applicant: K2M, Inc., Leesburg, VA (US)

(72) Inventor: Shyam Kishan, Indianapolis, IN (US)

(73) Assignee: K2M, Inc., Leesburg, VA (US)

( * ) Notice: Subject to any disclaimer, the term of this patent is extended or adjusted under 35 U.S.C. 154(b) by 53 days.

(21) Appl. No.: 14/731,886

(22) Filed: Jun. 5, 2015

(65) Prior Publication Data

US 2015/0351804 A1    Dec. 10, 2015

Related U.S. Application Data

(60) Provisional application No. 62/008,014, filed on Jun. 5, 2014.

(51) Int. Cl.
*A61B 17/70* (2006.01)
*A61B 17/56* (2006.01)

(52) U.S. Cl.
CPC ..... *A61B 17/7011* (2013.01); *A61B 2017/564* (2013.01)

(58) Field of Classification Search
CPC ............ A61B 17/7011; A61B 17/7013; A61B 17/7043; A61B 17/705; A61B 17/7053; A61B 17/7055; A61B 17/7067
See application file for complete search history.

(56) References Cited

U.S. PATENT DOCUMENTS

| 4,604,995 A * | 8/1986 | Stephens | A61B 17/7053 606/261 |
|---|---|---|---|
| 4,875,471 A | 10/1989 | Lea Plaza | |
| 2007/0233089 A1* | 10/2007 | DiPoto | A61B 17/7011 606/279 |
| 2007/0299445 A1* | 12/2007 | Shadduck | A61B 17/7011 606/86 A |
| 2008/0262552 A1* | 10/2008 | Kim | A61B 17/7011 606/276 |
| 2010/0036425 A1 | 2/2010 | Barrus et al. | |
| 2012/0065687 A1* | 3/2012 | Ballard | A61B 17/7004 606/259 |
| 2013/0245690 A1* | 9/2013 | Bridwell | A61B 17/7038 606/278 |

* cited by examiner

*Primary Examiner* — Julianna N Harvey
(74) *Attorney, Agent, or Firm* — Carter, DeLuca, Farrell & Schmidt, LLP

(57) ABSTRACT

A spinal rod includes a central connector and first and second legs. The central connector has first and second ends. The first leg has first, second, and third sections. The first section of the first leg is directly coupled to the first end of the central connector. The second leg has first, second, and third sections. The first section of the second leg is directly coupled to the second end of the central connector. The second leg is spaced apart from the first leg to define a gap therebetween. The spinal rod defines a longitudinal axis and each of the second sections is parallel to the longitudinal axis in first and second planes that are orthogonal to one another. The first plane passes through each of the second sections which are each offset from the longitudinal axis. The second plane passes through the central connector and bisects the spinal rod.

18 Claims, 3 Drawing Sheets

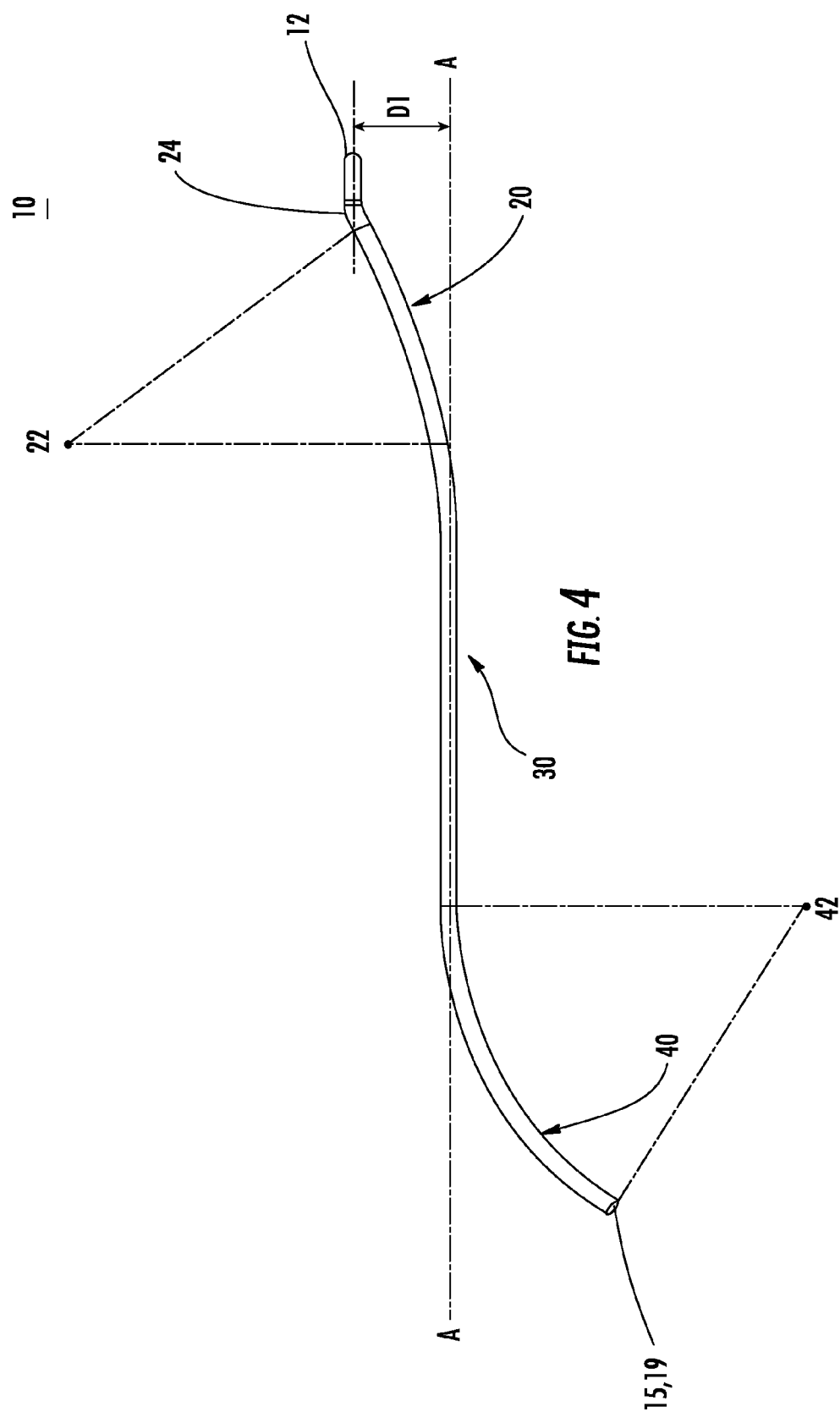

though the spinal
fusion may address the diseased or injured anatomy, the
natural biomechanics of the spine are affected in a unique
and unpredictable way.

BILATERAL CONTOURED ROD AND METHODS OF USE

CROSS-REFERENCE TO RELATED APPLICATION

This application claims the benefit of, and priority to, U.S. Provisional Patent Application Ser. No. 62/008,014, filed on Jun. 5, 2014, entire contents of which are hereby incorporated by reference.

BACKGROUND

1. Technical Field

The present disclosure relates to methods, systems, and apparatus for bony fixation and, more specifically, to methods, systems, and apparatus adapted for fixing the bones of the spine.

2. Discussion of Related Art

The human spine is comprised of thirty-three vertebrae and twenty-four as an adult. An infant contains 7 cervical vertebrae, 12 dorsal or thoracic vertebrae, 5 lumbar vertebrae, 5 sacral vertebrae, and 4 coccygeal or caudal vertebrae. In an adult, the 5 sacral vertebrae fuse together to form the sacrum and the 4 coccygeal vertebrae fuse to form the coccyx. Intervertebral discs lie between each pair of adjacent vertebrae. Every intervertebral disc maintains a space between adjacent vertebrae and acts as cushion under compressive, bending, and rotational loads and motions. Each intervertebral disc has a fibrocartilaginous central portion called the nucleus pulposus. The nucleus pulposus of a healthy intervertebral disc contains significant amount of water. This water content provides spongy quality and allows it to absorb spinal stress.

Each intervertebral disc has an annulus fibrosus, which condition might be affected by the water content of the nucleus pulposus. The annulus fibrosus consist of a ring of fibrocartilage and fibrous tissue forming the circumference of the intervertebral disc. Excessive pressure or injuries to the intervertebral discs may adversely affect the annulus fibrosus. Usually, the annulus fibrosus is the first portion of the intervertebral discs that is injured. The annulus fibrosus may be injured in several ways. Typically, the annulus fibrosus tears due to an injury. When these tears heal, scar tissue forms in the annulus fibrosus. Given that scar tissue is not as strong as normal ligament tissue, the annulus becomes weaker as more scar tissue forms. An annulus fibrosus with scar tissue is usually weaker than a normal annulus fibrosus. The formation of scar tissue may eventually lead to damage of the nucleus pulposus. As a result of this damage, the nucleus fibrosus may, for instance, lose water content, hindering the intervertebral disc's ability to act as a cushion. The reduced cushioning capability might increase stresses on the annulus fibrosus and, consequently, cause still more tears. Hence, the annulus fibrosus may undergo a degenerative cycle consisting of exponential reduction of water content. Eventually, the nucleus pulposus may lose all its water. As the nucleus pulposus loses its water content, it collapses and thus allows the vertebrae above and below the disc space to move closer to each other. In other words, the intervertebral disc space narrows as the nucleus pulposus loses water. When the nucleus pulposus collapses, the facet joints, which are located on the back of the spine, shift, altering the way these joints work together.

When a disc or vertebra is damaged due to disease or injury, performing a spinal fusion is one of the techniques used for treating the patient. During spinal fusion, a surgeon removes part or all of the intervertebral disc, inserts a natural or artificial disc spacer, and constructs an artificial structure to hold the affected vertebrae in place. While the spinal fusion may address the diseased or injured anatomy, the natural biomechanics of the spine are affected in a unique and unpredictable way.

SUMMARY

In an aspect of the present disclosure, a spinal rod includes a central connector, a first leg, and a second leg. The central connector has first and second ends. The first leg has first, second, and third sections. The first section of the first leg is directly coupled to the first end of the central connector. The second leg has first, second, and third sections. The first section of the second leg is directly coupled to the second end of the central connector. The second leg is spaced apart from the first leg to define a gap therebetween. The spinal rod defines a longitudinal axis and each of the second sections is parallel to the longitudinal axis in first and second planes that are orthogonal to one another. The first plane passes through each of the second sections which are each offset from the longitudinal axis. The second plane passes through the central connector and bisects the spinal rod. The central connector and the first and second legs may be of unitary construction or may be monolithically formed with one another.

In aspects, the first and second legs are identical to one another when viewed perpendicular to the second plane. Each of the first sections may be curved relative to the first plane and parallel to the second plane. Each of the first sections may include a first curve adjacent the central connector and a second curve adjacent the second section of the respective first and second legs.

In some aspects, each of the third sections is curved relative to the first and second planes. Each of the third sections may have a first end adjacent the second section of the respective one of the first and second legs. Each of the third sections may have a second end that is spaced apart from the second section of the respective one of the first and second legs. Each of the third sections may be curved away from the first and second planes from the first end to the second end.

In certain aspects, the central connector is parallel to the first plane. The central connector may be semi-circular.

In particular aspects, the first and second legs are configured to conform to a curvature of a spinal column. A curvature of the first section of the first and second legs may conform to a curvature of a thoracic region of the spinal column and a curvature of each of the third sections is configured to conform to a curvature of a lumbar region of the spinal column.

In an aspect of the present disclosure, a spinal rod includes a central connector, a first leg, and a second leg. The central connector has an arcuate configuration and includes first and second ends. The central connector is located in a first plane. The first leg has first, second, and third sections. The first section of the first leg is attached to the first end of the central connector and is monolithically formed therewith. The second leg has first, second, and third sections. The first section of the second leg is attached to the second end of the central connector and is monolithically formed therewith. The second sections are parallel to each other and are disposed in a second plane that is parallel to the first plane and is spaced therefrom. The first and second legs define a gap therebetween such that a distance between the first sections of the first and second legs is equal to a distance between the second sections of the first and second legs.

In an aspect of the present disclosure, a spinal rod includes a central connector, a first leg, and a second leg. The central connector has a first and second ends and is semi-circular therebetween. The first leg has first, second, and third sections. The first section of the first leg is unitarily formed with the first end of the central connector. The second leg has first, second, and third sections. The first section of the second leg is unitarily formed with the second end of the central connector. The second sections of the first and second legs are parallel to a longitudinal axis defined by the spinal rod in first and second planes that are orthogonal to one another. The first plane passes through the second sections of the first and second legs. The second plane passes through the central connector to bisect the spinal rod. The central connector is parallel to the first plane. The first section of each of the first and second legs is curved relative to the first plane and conformable to a curvature of a thoracic region of a spinal column and parallel to the second plane. The third section of each of the first and second legs is curved relative to the first and second planes and is conformable to a curvature of a lumbar region of the spinal column.

In another aspect of the present disclosure, a method of fixing a spinal column includes securing a first pair of pedicle screws in a first vertebra in a thoracic region of the spinal column and a second pair of pedicle screws in a second vertebra in a lumbar region of a spinal column and securing a first section of first and second legs of a spinal rod to heads of the first pair of pedicle screws, and securing a third section of the first and second legs to heads of the second pair of pedicle screws. One of each pair of the pedicle screws is positioned on one side of a spinal process of a respective vertebra and a second one of each pair of pedicle screws positioned on the other side of the spinal process of the respective vertebra. A central connect extending cephaladly from an end of each of the first and second legs and another end of each of the first and second legs extend caudally from the heads of the second pair of pedicle screws.

In aspects, the method includes conforming the rod to the thoracic region of the spinal column. Conforming the rod to the thoracic region of the spinal column may include adjusting a curvature of the first sections of the first and second legs.

In some aspects, the method includes conforming the rod to the lumbar region of the spinal column. Conforming the rod to the lumbar region of the spinal column may include adjusting a curvature of second sections of the first and second legs.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 4 is a side profile view of the spinal rod of FIG. 1.

DETAILED DESCRIPTION

Figure 1:
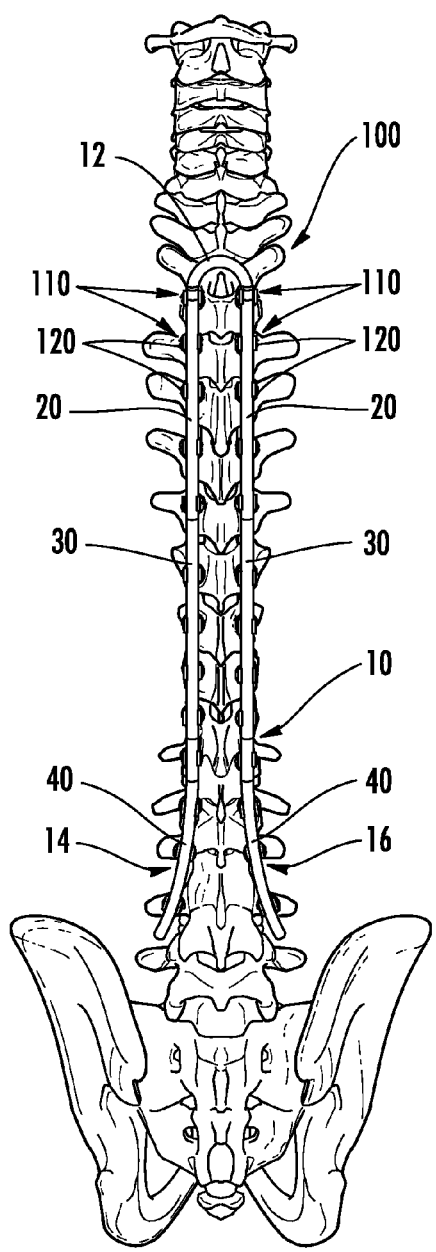
FIG. 1 is a posterior plan view of a spinal rod in accordance with the present disclosure fixed to a spinal column of a patient.

Embodiments of the present disclosure are now described in detail with reference to the drawings in which like reference numerals designate identical or corresponding elements in each of the several views. As commonly known, the term "clinician" refers to a doctor, a nurse or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is known to indicate a direction toward a patient's head, whereas the term "caudal" indicates a direction toward the patient's feet. Further still, the term "lateral" is understood to indicate a direction toward a side of the body of the patient, i.e., away from the middle of the body of the patient. The term "posterior" indicates a direction toward the patient's back, and the term "anterior" indicates a direction toward the patient's front. Additionally, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 2:
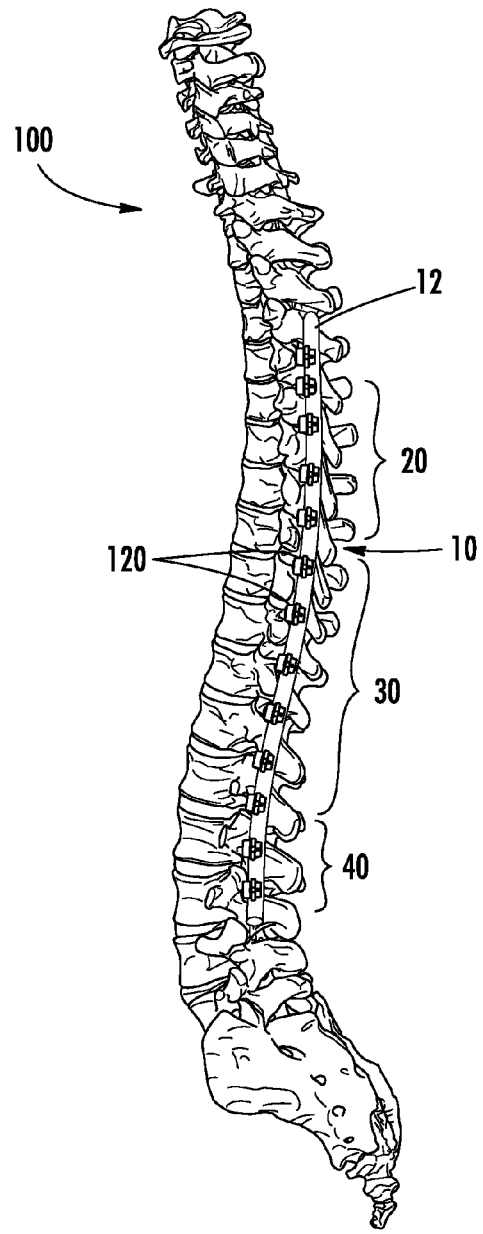
FIG. 2 is a side profile view of the spinal rod fixed to the spinal column of the patient of FIG. 1.

Referring now to FIGS. 1 and 2, a bilateral contoured rod 10 is provided in accordance with the present disclosure and is secured to a spinal column 100 of a patient. The rod 10 is secured to the spinal column 100 by a plurality of pedicle screws 110 fixed to vertebra of the spinal column 100 on both sides of spinal processes of the spinal column 100. As shown, the rod 10 is secured to the posterior side of the spinal column 100. To secure the rod 10 to each of the pedicle screws 110, the rod 10 is received within a head 120 of each pedicle screw 110. As shown, the rod 10 is secured to the heads 120 of the pedicle screw 110 with a tulip or taper-locking head. It is contemplated that the rod 10 may also be secured to the heads 120 by a set screw (not shown). Examples of pedicle screws with taper-locking heads are disclosed in U.S. Pat. No. 8,814,919 and examples of pedicle screws with rods secured by set screws are disclosed in U.S. Pat. No. 8,403,971, the entire contents of each of these disclosures hereby incorporated by reference.

Figure 3:
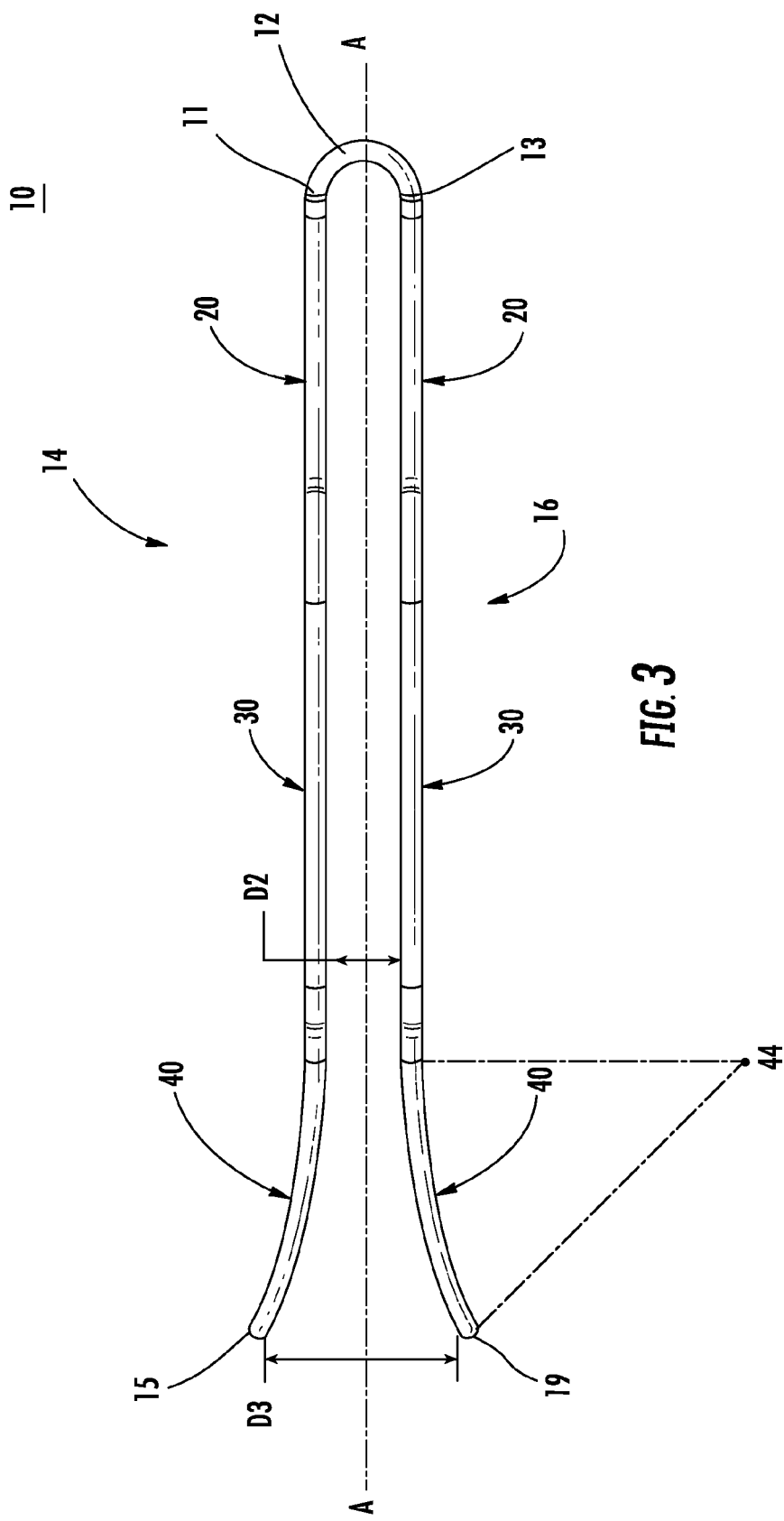
FIG. 3 is a posterior plan view of the spinal rod of FIG. 1.

With reference to FIGS. 3 and 4, the rod 10 includes a central connector or cephalad connector 12, a first leg 14, and a second leg 16. Each leg 14, 16 extends from a first or cephalad section 20 that is monolithically formed with the cephalad connector 12, through a second or central section 30, and to a third or caudad section 40. With particular reference to FIG. 3, the rod 10 is monolithically formed or is of unitary construction from a first end 15 of the rod 10 in the caudad section 40 of the first leg 14 to a second end 19 of the rod 10 in the caudad section 40 of the second leg 16. The rod 10 extends from the first end 15 at an end of the first leg 14 to the cephalad connector 12 and extends from the cephalad connector 12 the second end 19 at an end of the second leg 16.

With particular reference to FIGS. 2 and 4, the first and second legs 14, 16 are substantially similar in a side profile such that the rod 10 is sized and shaped to conform to or to define a curvature of a spinal column. Additionally or alternatively, the rod 10 is conformable to accommodate differences between patients. Specifically, the cephalad sections 20 are curved in a sagittal plane of a patient between the cephalad connector 12 and the central section 30 to conform to a thoracic region of a spinal column and the caudad sections 40 are curved in a sagittal plane and a coronal plane of a patient from the central section to the ends 15, 19 of the rod 10 to conform to a lumbar region of a spinal column. The central section 30 is substantially linear and parallel to a central longitudinal axis A-A of the rod 10.

A center of curvature 22 of the cephalad section 20 in a sagittal plane of a patient is above the central section 30 as shown in FIG. 4 and a center of curvature 42 of the caudad section 40 in the sagittal plane is below the central section as shown in FIG. 4. The caudad section 40 also has a center of curvature 44 in the coronal plane as shown in FIG. 3. It is contemplated that the center of curvature 42 and the center of curvature 44 may be the same or different points. The cephalad section 20 may include a transitional curvature 24 to transition into the cephalad connector 12. The transitional curvature 24 may have a radius of about 0.5 inches in a direction opposite the curvature of remainder of the cephalad section 20.

The central sections 30 define a central plane that passes through the central longitudinal axis A-A and each of the central sections 30. The central plane is configured to be parallel to a coronal plane of a patient. The cephalad connector 12 is substantially linear in the side profile and parallel to the central sections 30. The cephalad connector 12 is offset from the central longitudinal axis A-A and the central plane by a distance $D_1$. The distance $D_1$ is in a range of about 0.8 inches to about 1.6 inches.

With particular reference to FIG. 3, the first and second legs 14, 16 are offset from the central longitudinal axis A-A of the rod 10 to define a gap therebetween. The gap is substantially constant between the cephalad and central sections 20, 30 and increases between the caudad sections 40 reaching a maximum gap at the first and second ends 15, 19. Between the cephalad and central sections 20, 30 the gap has a distance $D_2$ and between the ends 15, 19 the gap has a distance $D_3$. The distance $D_2$ is in a range of about 0.750 to about 1.250 inches (e.g., about 1.000 inches). The distance $D_3$ is in a range of about 2.200 to about 3.200 inches (e.g., about 2.585 inches). The gap may increase as defined by a radius of curvature in a coronal plane of a patient.

The cephalad connector 12 has first and second ends 11, 13 and is arcuate therebetween. The cephalad connector 12 is in a plane parallel to the central plane. The first end 11 is connected to the cephalad section 20 of the first leg 14 and the second end 13 is connected to the cephalad section 20 of the second leg 16. The cephalad connector 12 is configured to wrap around a spinal process of a vertebra. As shown, the cephalad connector 12 defines a uniform semi-circular curve; however, it is contemplated that the cephalad connector 12 may include two corners and a backspan, a non-uniform curve, or any other structure for passing around or through a spinal process of a spinal column to connect the first and section legs 14, 16 together.

With reference to FIGS. 1 and 2, to install the rod 10 onto the spinal column of a patient, two pedicle screws 110 (FIG. 1) are secured in each vertebrae of the spinal column 100 on either side of the spinal processes for the regions to be secured to the rod 10 (e.g., vertebra in the thoracic and lumbar regions of the spinal column). A rod 10 is selected that defines a desired curvature of the spinal column of the patient (i.e., the first curvature selected to define the curvature of the thoracic region of the spinal column of the patient and the second curvature selected to define the curvature of the lumbar region of the spinal column). The rod 10 is then fixed to the head 120 of each pedicle screw 110 using known methods including, but not limited to, using a set screw or a tulip head. A rod reducer (not shown) may be used to position the rod 10 in the head of each pedicle screw 110.

It is contemplated that a rod 10 may be selected or adjusted to conform or fit to a spinal column of a patient. Specifically, cephalad sections 20 of the rod 10 may be selected or adjusted to conform or fit a curvature of a spine of a patient in a sagittal plane of a patient. In addition, the caudal sections 40 may be selected or adjusted to conform or fit a curvature of a spine of a patient in a sagittal plane and/or a coronal plane of a patient. The caudal section 40 may conform or fit a lumbar section of the spine of a patient. It is also contemplated that the caudal section 40 may extend into a sacral region of the spine of the patient. The caudal section 40 may be selected and/or adjusted to conform with a curvature of the spine of a patient in the sagittal plane and then separately selected or adjusted to conform with a curvature of the spine of the patient in the coronal plane of a patient (e.g., to fit around spinal processes of a lumbar and a sacral region of a patient).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A spinal rod comprising:
   a central connector having first and second ends;
   a first leg having a first section, a second section, and a third section, the first section of the first leg directly coupled to the first end of the central connector; and
   a second leg having a first section, a second section, and a third section, the first section of the second leg directly coupled to the second end of the central connector, the second leg spaced apart from the first leg to define a gap therebetween,
   wherein the central connector defines a uniform curve between the first and second ends, the curve being open in a direction towards the first and second legs and closed in a direction away from the first and second legs,
   wherein the spinal rod defines a longitudinal axis and each of the second sections are parallel to the longitudinal axis in first and second planes that are orthogonal to one another, the first plane passing through each of the second sections which are offset from the longitudinal axis, the second plane passing through the central connector to bisect the spinal rod, and
   wherein each of the third sections curve away from each of the first and second planes.

2. The spinal rod according to claim 1, wherein the central connector and the first and second legs are of unitary construction.

3. The spinal rod according to claim 1, wherein the central connector and the first and second legs are monolithically formed.

4. The spinal rod according to claim 1, wherein the first and second legs are identical to one another when viewed perpendicular to the second plane.

5. The spinal rod according to claim 1, wherein each of the first sections is curved relative to the first plane and parallel to the second plane.

6. The spinal rod according to claim 5, wherein each of the first sections includes a first curve adjacent the central connector and a second curve adjacent the second section of the respective first and second legs.

7. The spinal rod according to claim 1, wherein each of the third sections has a first end adjacent the second section of the respective one of the first and second legs and a second end spaced apart from the second section of the respective one of the first and second legs, each of the third sections curved away from the first and second planes from the first end to the second end.

8. The spinal rod according to claim 1, wherein the central connector is parallel to the first plane.

9. The spinal rod according to claim 1, wherein the central connector is semi-circular.

10. The spinal rod according to claim 1, wherein the first and second legs are configured to conform to a curvature of a spinal column.

11. The spinal rod according to claim 10, wherein a curvature of the first section of the first and second legs is configured to conform to a curvature of a thoracic region of the spinal column and a curvature of each of the third sections is configured to conform to a curvature of a lumbar region of the spinal column.

12. A spinal rod comprising:
a central connector having an arcuate configuration, the central connector including first and second ends, the central connector located entirely in a first plane;
a first leg having a first section, a second section, and a third section, the first section of the first leg attached to the first end of the central connector and monolithically formed therewith; and
a second leg having a first section, a second section, and a third section, the first section of the second leg attached to the second end of the central connector and monolithically formed therewith, wherein the second sections are parallel to each other and disposed in a second plane that is parallel to the first plane and spaced therefrom,
wherein the central connector extends from the first end in a direction away from the second section of the first leg in the first plane,
wherein the first and second legs define a gap therebetween, wherein a distance between the first sections of the first and second legs is equal to a distance between the second sections of the first and second legs, and wherein each of the third sections is curved such that a distance between the third sections of the first and second legs increases as distance from the second sections of the first and second legs increases.

13. A spinal rod comprising:
a central connector having first and second ends, the central connector being semi-circular from the first end to the second end;
a first leg having a first section, a second section, and a third section, the first section of the first leg being unitarily formed with the first end of the central connector; and
a second leg having a first section, a second section, and a third section, the first section of the second leg being unitarily formed with the second end of the central connector,
wherein the spinal rod defines a longitudinal axis and the second sections of the first and second legs are parallel to the longitudinal axis in first and second planes that are orthogonal to one another, the first plane passing through the second sections of the first and second legs, the second plane passing through the central connector to bisect the spinal rod, wherein the central connector is parallel to the first plane, wherein the first section of the first and second legs being curved relative to the first plane and conformable to a curvature of a thoracic region of a spinal column and parallel to the second plane, wherein the third section of the first and second legs is curved away from the first and second planes and conformable to a curvature of a lumbar region of the spinal column.

14. A method of fixing a spinal column comprising:
securing a first pair of pedicle screws in a first vertebra in a thoracic region of the spinal column and a second pair of pedicle screws in a second vertebra in a lumbar region of the spinal column, one of each pair of pedicle screws positioned on one side of a spinal process of the respective vertebra and a second one of each pair of pedicle screws positioned on the other side of the spinal process of the respective vertebra; and
securing a first section of first and second legs of a spinal rod to heads of the first pair of pedicle screws with a central connector extending cephaladly from an end of each of the first and second legs to define a uniform curve therebetween; and
securing a third section of the first and second legs to heads of the second pair of pedicle screws, ends of the first and second legs extending caudally and laterally from the heads of the second pair of pedicle screws.

15. The method according to claim 14, further comprising conforming the rod to the thoracic region of the spinal column.

16. The method according to claim 15, wherein conforming the rod to the thoracic region of the spinal column includes adjusting a curvature of first sections of the first and second legs.

17. The method according to claim 14, further comprising conforming the rod to the lumbar region of the spinal column.

18. The method according to claim 17, wherein conforming the rod to the lumbar region of the spinal column includes adjusting a curvature of second sections of the first and second legs.

* * * * *